United States Patent [19]

Tuchenhagen et al.

[11] 4,364,962

[45] Dec. 21, 1982

[54] METHOD FOR ENZYMATICALLY DECOMPOSING A LOW MOLECULAR WEIGHT MATERIAL

[75] Inventors: Jürgen Tuchenhagen, Vlotho-Uffeln; Franz Roiner, Barsinghausen; Josef Grosserhode, Frielingen, all of Fed. Rep. of Germany

[73] Assignee: Prof. Dipl.-KFM. Franz Poiner, Barsinghausen, Fed. Rep. of Germany

[21] Appl. No.: 276,819

[22] Filed: Jun. 24, 1981

Related U.S. Application Data

[63] Continuation of Ser. No. 102,850, Dec. 12, 1979, abandoned.

[30] Foreign Application Priority Data

Dec. 20, 1978 [DE] Fed. Rep. of Germany ....... 2855100

[51] Int. Cl.³ .................. A23C 9/12; A23C 9/142; A23C 9/146; A23C 21/02
[52] U.S. Cl. ........................... 426/41; 426/42; 426/43; 426/271; 426/491
[58] Field of Search ............. 426/34, 41, 42, 43, 426/491, 583, 271; 435/813, 95, 96

[56] References Cited

U.S. PATENT DOCUMENTS

| | | | |
|---|---|---|---|
| 3,720,583 | 3/1973 | Fisher | 435/95 |
| 3,911,140 | 10/1975 | Osborne et al. | 426/43 X |
| 4,091,116 | 5/1978 | Edwards et al. | 426/491 X |

OTHER PUBLICATIONS

Klostermeyer, et al., Lactose Treatment of Skim Milk for the Production of Lactose-Reduced Skim Milk Powder, Kieler Milch-Mirtschaffliche Forschungsherichye, vol. 30, No. 3, 1978 (pp. 295-340).
Porter, et al., Membrane Ultrafiltration Chem. Tech. Jan. 1972 (pp. 56-61).
Zaborsky, O., Immobilized Enzymes, CRC Press, Cleveland, Ohio, 1973 (pp. 103-115).

*Primary Examiner*—David M. Naff
*Attorney, Agent, or Firm*—Fleit & Jacobson

[57] ABSTRACT

A low molecular weight material such as lactose in an aqueous polydispersed system such as milk is enzymatically decomposed by fermentation with enzyme preparations and/or microorganisms, the decomposition products are separated such as by ultrafiltration and the remaining solution is at least partially returned to the starting aqueous system. In a specific embodiment, lactose in milk or whey is decomposed to saccharides and lactic acid by fermenting with an enzyme preparation that splits lactose to saccharides and a microorganism that ferments lactose to lactic acid, separating the saccharides and lactic acid produced, recycling the remaining solution to the starting milk or whey, separating lactic acid from the saccharides and recycling the saccharides to the starting whey or milk. By this process, the lactose content can be partially or completely removed, lactic acid can be produced in pure form, an optimum pH can be maintained during fermentation and a sweet concentrate having 0% or reduced lactose content can be produced.

11 Claims, No Drawings

METHOD FOR ENZYMATICALLY DECOMPOSING A LOW MOLECULAR WEIGHT MATERIAL

This is a continuation of application Ser. No. 102,850 filed Dec. 12, 1979, now abandoned.

The invention relates to a method for partially or fully enzymatically decomposing a low molecular weight material such as lactose in an aqueous polydispersed system of low molecular weight and high molecular weight materials such as milk, curdled milk, sour cream, buttermilk, whey, permeated (processed) milk and the like or mixtures thereof.

A polydispersed system having water as the continuous phase and more or less high proportions of high molecular weight and low molecular weight materials distributed therein is milk or a milk-like system. One of the low molecular weight materials therein is lactose, a disaccharide, namely at a very high percentage compared with the proportions of the other dispersed materials. In its initial form, lactose has a reduced sweetening effect and is also incompatible for many human beings (lactose malabsorption).

In the dairy industry as well as in processes for making foodstuffs (sour vegetables, yeast, cooked meat, etc.), two basic methods are available for changing the lactose and these are described in the paper by H. Klosermeyer, E. Herlitz, R. H. Jürgens, E. H. Reimerdes and J. Thomasow, 'Lactose Treatment of Skim Milk for the Production of Lactose-Reduced Skim Milk Powder' published in Kieler Milchwirtschaftlicher Forschungsberichte, 1978, No. 3, pages 295 et seq.

1. Fermentation of the lactose and conversion to lactic acid in a predominantly homofermentative process using lactose-fermenting lactic acid-forming microorganisms. The microorganisms receive the necessary enzymes, thereby ferment the lactose and immediately convert the fermentation products as formed into lactic acid. The lactic acid is thus a product of metabolism.

2. Fermentation of the lactose by the precise use of enzymes which were previously isolated from microorganism cultures in a special process. In this case microorganisms are no longer used directly and consequently this process fails to produce lactic acid; the lactose is merely split up.

Both methods have considerable disadvantages.

A common disadvantage is that the conversion as well as the decomposition products of the lactose remain in the starting system as additional dispersed materials. In the case of method 1, this means:

Microorganisms of known species or mixed cultures are intensively mixed with the starting system, e.g. milk, curdled milk, buttermilk, whey, permeated milk, mixtures thereof, etc., and are cultured by known methods. The microorganisms use the lactose as a nutrient in that they first split the lactose with the aid of enzymes that immediately use the fission products for their own nutrition. Acid is finally produced as a product of metabolism. If the process is carried out correctly, the predominant product is lactic acid. By means of suitable measuring methods, this process can be monitored, i.e. the pH value in the starting system drops from, say, pH 6.5 to pH 4.5 or until the products of metabolism cause the microorganisms to become self-restrained. When this self-restraint has taken place, the lactose in the starting system is in this case partially reduced, i.e. by about 1%, but lactic acid has been introduced in the system to the same ratio.

Now, methods are known to displace the self-restraint of the microorganisms in the described process and thereby make it possible to decompose a higher percentage of lactose or to achieve a higher percentage of lactic acid. However, at all times all the starting materials as well as lactic acid are contained in the system and are upgraded during subsequent concentrating processes. If a separating process such as ultra-filtration is interposed, the high molecular weight materials are separated but the low molecular weight materials continue to remain in the system and are again upgraded.

If this process is applied to milk, the latter cannot be upgraded because the albumen is destabilized on account of the lactic acid that is formed. In this case the system consists of all the component materials that were initially present, only the proportion of lactose having been slightly reduced with the proportion of acid having been increased.

In the case of method 2, lactose is split into monosaccharides by the precise introduction of enzyme preparations.

One known method consists of adding the enzyme to the dispersion without recovering it. This has the technical disadvantage of being expensive and introducing an undesirable substance in the case of foodstuffs.

A second known method works with dissolved enzymes in a membrane chamber through which an ultra-filtrate of the dispersion flows. Apart from the cost of membrane technology, it is a disadvantage that the membranes become blocked by deposits of the contents of the dispersion because it is not possible to operate under sterile conditions. Consequently, the membrane fillings deteriorate.

A third known method works with immobilised enzymes through which a substrate flows. In this case it is not possible to fix sufficient activity on the carrier. Also, the available activity only has a limited life because there is no resistance to abrasion. The attempt to achieve abrasion resistance by embedding porous sponge-like glass balls or swellable gels in the interior does not lead to satisfactory results because this creates the danger of self-restraint through inadequate discharge of the products of decomposition.

The invention is based on the problem of improving the known methods by providing a method of the aforementioned kind that is not associated with self-restraint and wear phenomena of the enzyme preparations or microorganism cultures.

According to the invention, this problem is solved in that (A) microorganisms decomposing the low molecular weight material are admixed with the aqueous polydispersed system, the substances formed during metabolism of the low molecular weight material are separated, and the materials remaining in the residual solution of the polydispersed system are partially or completely fed to the starting solution, or (B) microorganisms decomposing the low molecular weight material and/or enzyme preparations and the aqueous polydispersed system are brought into contact while spatially separated, the substances formed during metabolism of the low molecular weight material are separated, and the materials remaining in the residual solution of the polydispersed system are partially or completely fed to the starting solution.

Other features of the invention are characterised in the subsidiary claims.

The advantages achievable by the invention are that no self-restraint and no wear occur for the microorganisms of the enzyme preparations. Since the fermented portion such as the lactate in the case of treating milk, or milk-like products is continuously or progressively removed from the starting system, the pH value of the milk can be kept in a range that is optimum for the microorganism culture or enzyme preparations. Further, it is possible to reduce the lactose content of the starting medium down to 0% and thereby achieve a starting product that is completely new for the purpose of foodstuff technology. Further, it is for example possible to obtain the product of metabolism, namely lactic acid, in pure form. A furher advantage is that one can achieve complete separation between the dispersion to be treated and the enzyme preparation or microorganism cultures. By adding the dispersion from which the products of decomposition have been removed to the starting dispersion, it is possible always to work in an optimum pH or SH range. It is also possible to combine with the process a concentration method so that the lactose content in the starting medium to be fermented is for a very long time kept in the original proportion and this, in turn, ensures that fermentation will be an optimum. Still further, it is possible to exercise control over the process by means of different pressures in the parts containing the dispersion to be treated or the enzyme preparation or microorganism cultures. Nor is any large technological expense necessary because it is possible to use for example conventionally marketed tubes which are known to have walls which are permeable to molecules up to a particular size. An additional advantage is the fact that no specially prepared enzymes must be used.

Three examples of the invention will now be described in relation to the decomposition of lactose.

EXAMPLE 1

Milk with a fat content of less than 0.1% fat is to serve as the sugar-containing aqueous polydispersed system.

The starting material is brought to a fermentation temperature of, for example, 44° C. and a bacillus culture is admixed with it as the fermentation agent. The fermentation process commences. After reaching a pH or SH value of, for example, 6.0 pH or about 10 SH suitable for the fermentation process, the polydispersed system is subjected to a separating process, e.g. ultra-filtration. Two partstrains are obtained, namely the retained flow and the permeated flow. The retained portion (a residual solution of the aqueous polydispersed system) is immediately returned to the fermentation vessel, while the permeated portion (a further residual solution of the aqueous polydispersed system) is for example subjected to a neutralization process, e.g. an ion exchange process, and returned to the starting milk after neutralization. The pH value or the SH value can be kept constant during this stage of the process so that the fermentation process will be an optimum until the desired degree of sugar removal or complete removal of the sugar from the starting medium has been achieved.

If ion exchange is employed for the neutralization step, then the fermentation product is produced during regeneration of the ion exchanger and this is subjected to a suitable method such as vaporization to increase the concentration.

EXAMPLE 2

Whey with a lactose content of about 4.5%, a salt content of about 0.75% and an albumen content of about 0.6% is desaccharified in a completely continuous process.

A thermally insulating double tube of which the inner tube is permeable in both directions for the lactose in solution but impermeable to the enzyme for splitting the lactose has its inner tube supplied with the enzyme. Whey flows in the outer tube.

The enzymatic process is started in that lactose enters the inner tube through its wall and the disaccharide is split into the appropriate monosaccharides.

Whey is removed from the outer tube at a suitable position and the split sugar is removed from the solution, e.g. by a crystallization method. An albumen-salt solution is left and this can be treated further depending on its intended use.

It is also conceivable to remove salt from the whey during the enzymatic process or prior thereto, e.g. by a dialysis method, and to feed the desalinated solution which still contains sugar and albumen to the enzymatic process for the purpose of controlling the latter.

EXAMPLE 3

Desugarizing milk and producing a sweet-hour concentrate.

Skim milk having a lactose content of about 4.8%, an albumen content of about 3.4% and a salt content of about 0.8% is brought to reaction temperature in a fermenting vessel. A tube material permeable to lactose solutions and lactic acid solutions is introduced in the fermenting vessel in which the fermentation agent (microorganisms and enzyme preparation) is contained. Two processes are initiated:

1. Enzymatic lactose splitting; and
2. Fermentation, reduction of lactose to form lactic acid.

To achieve a fermentation process that is as rapid as possible, the fermentation agents as well as the polydispersed system are kept in motion; also, after a starting period the skim milk which is in a state of fermentation is partly subjected for example to ultrafiltration for the purpose of removing protein. The retained portion (first residual solution of the aqueous polydispersed system) is recycled to the decomposing process, while the permeated portion is subjected to a further separating process, e.g. ion exchange. The anion, lactic acid, is thereby separated. The permeated portion (further residual solution of the aqueous polydispersed system) separated from the lactic acid is then returned to the fermentation process as a neutralization agent. This process takes place until the original proportion of sugar has been decomposed into certain proportions of lactic acid and monosaccharides. The proportions depend on the intended use. Following completion of the enzymatic decomposition, two products are present:

1. A completely or partially desaccharified concentrated albumen solution which can be processed to form further products; and
2. A sweet-sour desalinated concentratable aqueous solution.

We claim:
1. A method for enzymatically decomposing lactose in an aqueous polydispersed system selected from the group consisting of milk, skimmilk, curdled milk, whey, sour cream, buttermilk, permeated milk, and mixtures thereof, the polydispersed system having a high molecular weight component and a low molecular weight componenet containing lactose, said method comprising the steps of:
- (a) contacting the lactose with an enzyme preparation that splits lactose to saccharides and a microorganism that ferments lactose to lactic acid;
- (b) separating the low molecular weight component containing decomposition products of lactose comprising saccharides and lactic acid from the high molecular weight component;
- (c) recycling at least a portion of the high molecular weight component from step (b) to step (a); and
- (d) separating lactic acid from the low molecular weight component containing saccharides and lactic acid and recycling the residual low molecular weight component containing saccharides to step (a);
- (e) repeating steps (a) through (d) until the amount of lactose in the polydispersed system has been reduced to a predetermined level; and
- (f) recovering a polydispersed system of reduced lactose content.

2. The method of claim 1 in which the aqueous polydispersed system and the microorganism are flowed toward each other.

3. The method of claim 1 in which the saccharides and lactic acid formed during step (a) are continuously removed from the polydispsersed system.

4. The method of claim 1 in which the saccharides and lactic acid formed by step (a) are progressively removed from the polydispersed system.

5. The method of claim 1 in which the saccharides and lactic acid formed during step (a) are separated after neutralization.

6. The method of claim 1 in which the saccharides and lactic acid formed during step (a) are separated after a change in concentration.

7. The method of claim 1 in which the aqueous polydispersed system is concentrated after saccharides and lactic acid are formed in step (a).

8. The method of claim 1 in which the microorganisms for fermenting lactose to lactic acid are admixed with the aqueous polydispersed system.

9. The method of claim 1 in which the microorganisms for fermenting lactose to lactic acid and the lactose are contacted while the microorganisms and the aqueous polydispersed system are spatially separated by a semi-permeable membrane.

10. The process of claim 1, wherein the low molecular weight component containing decomposition products of lactose is separated from the high molecular weight component by ultrafiltration.

11. A method for enzymatically decomposing lactose in an aqueous polydispersed system selected from the group consisting of milk, skimmilk, curdled milk, whey, sour cream, buttermilk, permeated milk or mixtures thereof, the polydispersed system having a high molecular weight component and a low molecular weight component containing lactose, comprising the steps of:
- (a) contacting the lactose with an enzyme preparation that splits lactose to saccharides and a microorganism that ferments lactose to lactic acid, said microorganism being spatially separated from the aqueous polydispersed system by a membrane permeable to lactose;
- (b) separating the low molecular weight component containing decomposition products of lactose comprising saccharides and lactic acid from the high molecular weight component;
- (c) recycling at least a portion of the high molecular weight component from step (b) to step (a);
- (d) separating lactic acid from the low molecular weight component containing saccharides and lactic acid and recycling the residual low molecular weight component containing saccharides to step (a);
- (e) repeating steps (a) through (d) until the amount of lactose in the polydispersed system has been reduced to a predetermined level; and
- (f) recovering a polydispersed system of reduced lactose content.

* * * * *